United States Patent [19]

Strong et al.

[11] Patent Number: 5,281,713
[45] Date of Patent: Jan. 25, 1994

[54] PROCESS FOR THE MANUFACTURE OF 2-ALKOXYMETHYLACROLEIN

[75] Inventors: Henry L. Strong, Somerset, N.J.; David A. Cortes, Fairless Hills, Pa.; Zareen Ahmed, Princeton Junction, N.J.

[73] Assignee: American Cyanamid Company, Wayne, N.J.

[21] Appl. No.: 961,471

[22] Filed: Oct. 23, 1992

Related U.S. Application Data

[63] Continuation-in-part of Ser. No. 812,518, Dec. 20, 1991, Pat. No. 5,177,266.

[51] Int. Cl.$^5$ .................................... C07D 215/24
[52] U.S. Cl. .................................... 546/179; 546/178; 568/460
[58] Field of Search .................. 546/178, 179, 250; 568/460

[56] References Cited

U.S. PATENT DOCUMENTS

| | | | |
|---|---|---|---|
| 4,065,455 | 12/1977 | Mattison | 546/179 |
| 4,552,985 | 11/1985 | Merger et al. | 568/497 |
| 4,723,011 | 2/1988 | Doehner, Jr. | 546/250 |
| 4,948,896 | 8/1990 | Nagao | 546/250 |
| 5,008,392 | 4/1991 | Meier et al. | 546/250 |
| 5,177,266 | 1/1993 | Strong | 568/460 |

FOREIGN PATENT DOCUMENTS

| | | | |
|---|---|---|---|
| 0350691A2 | 7/1988 | European Pat. Off. | 546/250 |
| 0363818A1 | 10/1988 | European Pat. Off. | 546/250 |

*Primary Examiner*—Werren B. Lone
*Attorney, Agent, or Firm*—Peggy Ann Climenson

[57] ABSTRACT

There is provided a process for the manufacture of 2-alkoxymethylacrolein compounds via the reaction of an appropriate alcohol and acrolein in the presence of an acid and a trisubstituted amine to form an intermediate and the subsequent reaction of the intermediate with formaldehyde in the presence of an acid and a disubstituted amine. There is also provided a process for the manufacture of 3-alkoxymethylquinolines from 2-alkoxymethylacrolein.

5 Claims, No Drawings

PROCESS FOR THE MANUFACTURE OF 2-ALKOXYMETHYLACROLEIN

This is a continuation-in-part of copending application Ser. No. 07/812,518 filed on Dec. 20, 1991 U.S. Pat. No. 5,177,266.

BACKGROUND OF THE INVENTION

Although there are literature procedures which have been used successfully to prepare certain substituted acrolein compounds, there is, as yet, no known method reported for the manufacture of 2-alkoxy methylacrolein.

Alpha, beta-unsaturated aldehydes such as 2-alkoxymethylacrolein are useful in the preparation of substituted pyridine-2,3-dicarboxylates, which are key intermediates in the manufacture of a new class of imidazolinone herbicides. The use of $\alpha,\beta$-unsaturated aldehydes in the preparation of pyridine-2,3-dicarboxylates is described in U.S. Pat. Nos. 4,723,011, 4,948,896 and 5,008,392.

Therefore, it is an object of this invention to provide a convenient and effective method for the manufacture of 2-alkoxymethylacrolein compounds useful in the preparation of the herbicide intermediates.

SUMMARY OF THE INVENTION

The present invention relates to a process for the manufacture of compounds of formula I

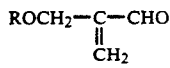  (I)

wherein R is $C_1$ to $C_6$alkyl.

The formula I alkoxymethylacrolein compound is prepared by reacting an alcohol, ROH wherein R is as described for formula I, with at least one molar equivalent of acrolein in the presence of an acid, a catalytic amount of a trisubstituted amine and a solvent to form an intermediate and reacting said intermediate with at least one molar equivalent of formaldehyde in the presence of an acid, a catalytic amount of disubstituted amine and a solvent to obtain the desired formula I compound.

The invention further relates to a process for the manufacture of 2-alkoxymethylacrolein compounds of formula I which comprises reacting a suitable compound of formula II

  (II)

wherein R is as described for formula I and W is CHO or $CH(OR_1)_2$ and $R_1$ is $C_1$ to $C_4$alkyl, with at least one molar equivalent of formaldehyde in the presence of an acid, a catalytic amount of a disubstituted amine and a solvent.

The invention also relates to the use of compounds of formula I in the manufacture of important quinoline and pyridine herbicidal intermediates.

DESCRIPTION OF THE INVENTION

The present invention provides a process for the manufacture of compounds of formula I. The compounds of formula I may be used to prepare 3-alkoxymethylquinolines and 5-alkoxymethylpyridine-2,3-dicarboxylates which are key intermediate compounds in the preparation of 2-(imidazolin-2-yl)nicotinate herbicides. For example, the formula I compounds of the present invention may be used to prepare 3-alkoxymethylquinolines of formula III

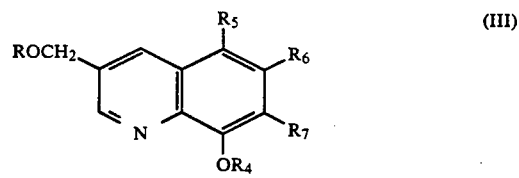

wherein
R is $C_1$–$C_6$alkyl;
$R_4$ is hydrogen or $C_1$–$C_4$alkyl; and
$R_5$, $R_6$ and $R_7$ are each independently hydrogen or $OR_4$.

3-Alkoxymethylquinolines may be prepared by reacting a substituted aniline of formula IV with at least one molar equivalent of a 2-alkoxymethylacrolein of formula I in the presence of an acid and a solvent and optionally in the presence of a substituted nitrobenzene of formula V, preferably at an elevated temperature, to form desired formula III compounds. The above reaction scheme is shown in flow diagram I.

FLOW DIAGRAM I

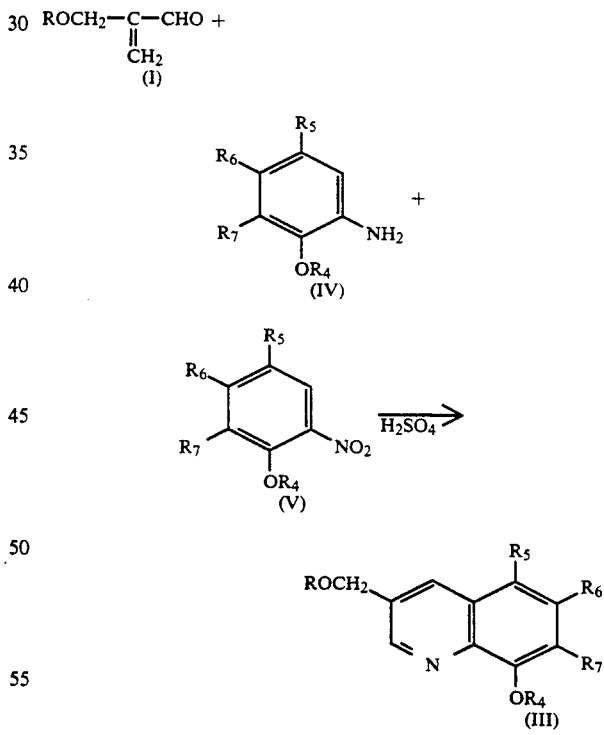

Acids suitable for use in the process used to prepare formula III compounds are strong organic and mineral acids such as sulfuric acid, phosphoric acid and hydrochloric acid. Solvents suitable for use in the process used to prepare formula III compounds are water and ROH alcohols wherein R is $C_1$–$C_6$alkyl. Preferred solvents are ROH alcohols wherein R corresponds to the R of the formula I compound with methanol being a most preferred solvent. Reaction temperatures of from about 30° C. to 120° C., preferably about 50° C. to 110°

C., are suitable for use in the process used to prepare formula III compounds.

The thus-obtained formula III 3-alkoxymethylquinoline compounds may be oxidized to form 5-alkoxymethylpyridine-2,3-dicarboxylic acids of formula VI. The above reaction scheme is shown in flow diagram II.

FLOW DIAGRAM II

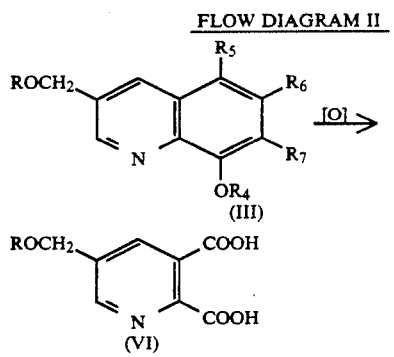
(III)
(VI)

Among the methods suitable to oxidize formula III compounds to formula VI compounds are nitric acid oxidation, base peroxide oxidation, base peroxide followed by sodium hypochlorite oxidation, chlorate catalyzed by vanadium oxidation, ozone oxidation and the like.

The thus-obtained formula VI 5-alkoxymethylpyridine-2,3-dicarboxylic acids may be converted to the corresponding herbicidal 2-(imidazolin-2-yl)nicotinic acids, esters and salts described in co-pending application Ser. No. 397,699, filed on Aug. 23, 1989.

Advantageously, the formula I compounds of the present invention may also be reacted with an α-halo-β-keto ester in the presence of an ammonium salt to form the corresponding pyridine-2,3-dicarboxylate product described in U.S. Pat. No. 4,723,011 and shown in flow diagram III.

Flow Diagram III

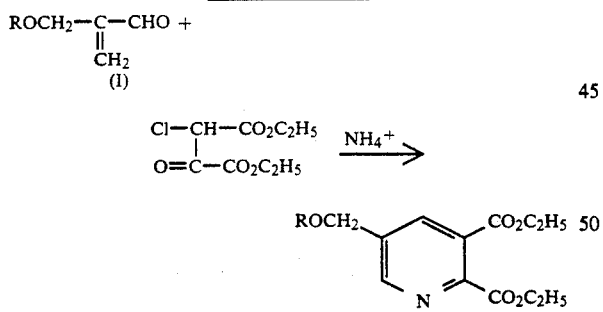

Further, 2-alkoxymethylacrolein compounds of formula I may be reacted with a dialkyl dihalomaleate in the presence of ammonia to form the desired pyridinedicarboxylate product described in U.S. Pat. No. 5,008,392 and shown in flow diagram IV.

Flow Diagram IV

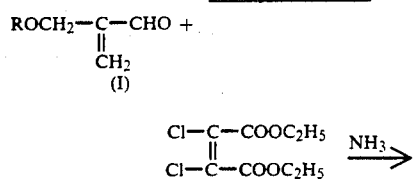

-continued
Flow Diagram IV

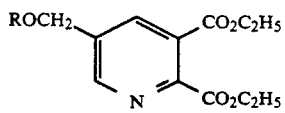

The thus-obtained pyridinedicarboxylate compounds may be converted to the corresponding herbicidal 2-(imidazolin-2-yl)nicotinic acids, esters and salts described in U.S. Pat. No. 4,798,619 and co-pending application Ser. No. 397,699, filed on Aug. 23, 1989.

Compounds of formula I are difficult to prepare using the Mannich-type conditions set forth in *Synthesis*, pp. 703-775 (1973). It has now been found, that the alkoxymethyl compounds of formula I may be effectively prepared in an efficient process from readily available starting materials. In accordance with the method of invention, an appropriate alcohol having the formula, ROH wherein R is $C_1$ to $C_6$ alkyl, may be reacted with at least one molar equivalent of acrolein in the presence of an acid, a catalytic amount of a trisubstituted amine and a solvent to form an intermediate and the intermediate may be reacted with at least one molar equivalent of formaldehyde in the presence of an acid, a disubstituted amine and a solvent to form the desired formula I alkoxymethylacrolein compound. The reaction is shown in flow diagram V.

Flow Diagram V

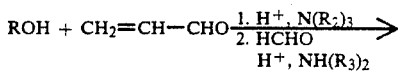

$$ROCH_2-\underset{\underset{CH_2}{\|}}{C}-CHO$$
(I)

In general, the formation of the intermediate and the formula I product are temperature dependent, that is, increased reaction temperature increases the rate of formation. Convenient reaction times may be obtained by increasing the reaction temperature to about 20° to 110° C., preferably about 75° to 100° C. Suitable reaction solvents are water or mixtures of water and a water-miscible organic solvent. Acids suitable for use in the present process are strong mineral acids, preferably polybasic acids such as sulfuric acid and phosphoric acid. Trisubstituted amines, $N(R_2)_3$, wherein $R_2$ is $C_1$-$C_4$alkyl, $C_1$-$C_4$alkanol and the like are suitable for use in the present invention. Disubstituted amines, $NH(R_3)_2$, wherein $R_3$ is $C_1$-$C_6$alkyl, preferably dibutylamine, may be used in the inventive process. It is intended formaldehyde be used in any of its readily available forms and preferably as an aqueous solution of about 37% concentration.

Advantageously, compounds of formula I may also be prepared by reacting a compound of formula II

wherein R is $C_1$-$C_6$alkyl and W is CHO or $CH(OR_1)_2$ and $R_1$ is $C_1$-$C_4$alkyl, with at least one molar equivalent of formaldehyde in the presence of an acid, a catalytic amount of a disubstituted amine, $NH(R_3)_2$ wherein $R_3$ is $C_1$–$C_4$ alkyl, and a solvent. The reaction is shown in flow diagram VI.

Flow Diagram VI

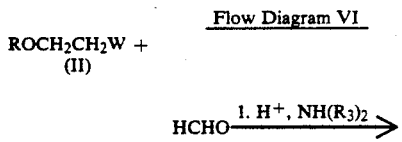

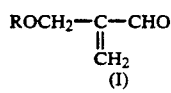

Compounds of formula II may be prepared according to methods known in the art such as that described by R. Hall and E. S. Stern, *Journal of the Chemical Society* (London), pp. 3388–3393 (1954). The formaldehyde employed in the above process may be in any of its readily available forms and preferably as an aqueous solution of about 37%. Acids suitable for use are strong mineral acids such as those mentioned hereinabove and preferably sulfuric acid or phosphoric acid. The reaction is temperature dependent, therefore convenient reaction times may be obtained by elevating the reaction temperature to about 20° to 110° C., preferably about 75° to 100° C.

In order to present a more clear understanding of the invention, the following examples are set forth. The examples are primarily for the purpose of demonstrating more specific details thereof and the invention is not to be limited thereby except as defined in the claims.

Unless otherwise noted, all parts are parts by weight. The term NMR designates nuclear magnetic resonance spectroscopy.

EXAMPLE 1

Preparation of 3-(Methoxymethyl)-8-quinolinol

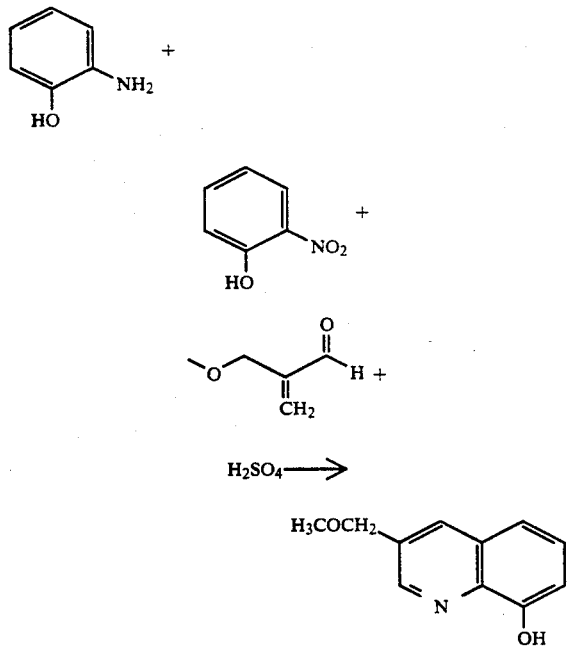

A solution of methanol and sulfuric acid (10.0 g, 0.1 mol) is heated to 65° C., treated with o-aminophenol (4.36 g, 0.04 mol) and o-nitrophenol (2.78 g, 0.02 mol), heated to 70° C., treated with methoxymethacrolein (6.0 g, 0.06 mol) over 40 minutes at 85° to 90° C. and diluted with water. The aqueous mixture is adjusted to about pH 2 with 50% sodium hydroxide solution and filtered. The filtrate is adjusted to about pH 7 with 50% sodium hydroxide solution and extracted with chloroform. The combined organic extracts are concentrated in vacuo to give the title product as a solid which is identified by $^1$H and $^{13}$CNMR spectral analyses.

Using essentially the same procedure, but substituting o-anisidine for o-aminophenol, 8-methoxy-3-(methoxymethyl)quinoline is obtained.

EXAMPLE 2

Preparation of 5-(Methoxymethyl)-2,3-pyridinedicarboxylic acid

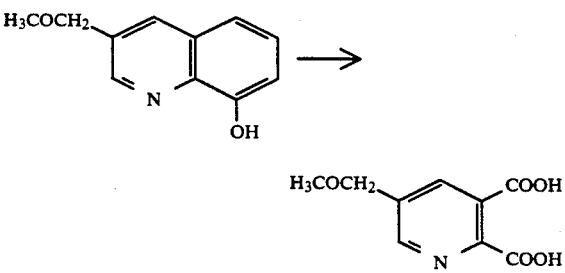

A mixture of 3-(methoxymethyl)-8-quinolinol (0.92 g, 4.9 mmol) in water is treated with 50% sodium hydroxide solution (1.0 g real, 25.0 mmol), heated to 85° C. and treated with 30% hydrogen peroxide solution (3.4 g real, 100.0 mmol) over 2 hours while maintaining the temperature between 65°–90° C. The reaction mixture (26.0 g) is then cooled to room temperature, assayed by HPLC and found to contain 3.15% of the title product (80% yield).

EXAMPLE 3

Preparation of Dimethyl 5-(methoxymethyl)-2,3-pyridinedicarboxylate

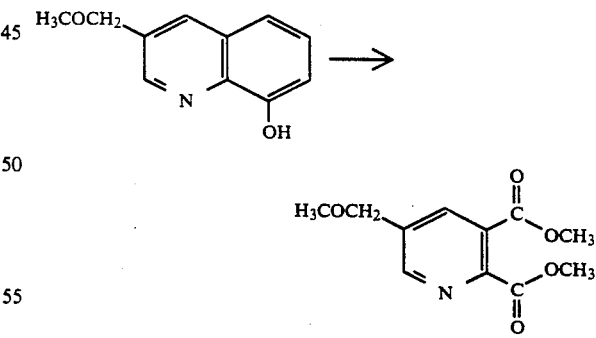

Ozone is bubbled through a solution of 3-(methoxymethyl)-8-quinolinol (0.145 g, 0.78 mmol) in 90% acetic acid at room temperature. After 20 minutes, the reaction mixture is concentrated in vacuo and the resulting solid is dissolved in 95% ethanol and treated with excess diazomethane. After stirring at room temperature for 14 hours, the reaction mixture is treated with acetic acid and concentrated in vacuo to give a yellow oil. Flash chromatography of the oil using silica gel and a 4:1 to 2:1 hexanes/ethyl acetate solution gives the title product as a colorless oil, 0.072 g (41% yield), which is identified by ¹H and ¹³CNMR spectral analyses.

EXAMPLE 4

Preparation of Methyl 3-formyl-5-(methoxymethyl)picolinate

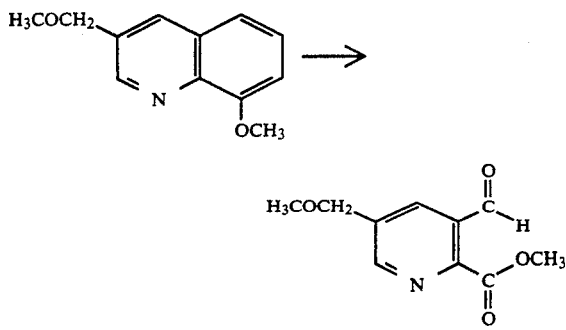

Ozone is bubbled through a solution of 8-methoxy-3-(methoxymethyl)quinoline (0.134 g, 0.66 mmol) in a 9:1 acetonitrile/water mixture at 0° C. After 10 minutes, the reaction mixture is concentrated in vacuo and the resulting oil is dissolved in methanol and treated with excess diazomethane. After stirring for 14 hours at room temperature, the reaction mixture is treated with acetic acid and concentrated in vacuo to obtain a red oil. Flash chromatography of the oil using silica gel and a 3:1 hexanes/ethyl acetate mixture gives the title product as a colorless oil which is identified by ¹HNMR spectral analysis.

Using essentially the same procedure, but substituting 90% acetic acid for the 9:1 acetonitrile/water mixture, the title product is obtained as a colorless oil which is identified by ¹HNMR spectral analysis.

EXAMPLE 5

Preparation of 2-methoxymethylacrolein from acrolein

A stirred mixture of acrolein (112 g, 2.0 mole), methanol (310 g, 9.08 mole), triethanolamine (7.5 g, 0.05 mole) and 85% phosphoric acid (5.7 g, 0.049 mole) in water is heated at reflux temperature for 9 hours, cooled to room temperature and filtered. The filtrate is diluted with water and treated with a 37% formaldehyde solution (162 g, 2.0 mole formaldehyde), concentrated sulfuric acid (11.6 g, 0.11 mole), and dibutylamine (27 g, 0.21 mole), heated at reflux temperature for 4 hours, cooled to room temperature and extracted with methylene chloride. The extracts are combined and concentrated and the concentrate is vacuum distilled to give the title product, 88 g (44% yield) bp 64°-66°/70 mm Hg, identified by NMR analysis.

EXAMPLE 6

Preparation of 2-ethoxymethylacrolein from acrolein

A stirred mixture of anhydrous ethanol (235.5 g, 5.12 mole) and acrolein (77.3 g, 1.38 mole) is treated with 0.7 ml concentrated HCl and NH₄Cl (6.0 g, 0.11 mole) and heated to reflux temperature over a 3 hour period. The reaction mixture is heated at reflux temperatures for 18 hours in a flask fitted with a 1 Dean Stark trap. The trap is removed and the reaction mixture is vacuum distilled. The distillate is redistilled, and 42 g is added to a stirred mixture of water, 0.8 g of concentrated H₂SO₄, hydroquinone (0.05 g, 0.45 mmole) and dibutylamine (1.78 g, 0.014 mole). A 37% formaldehyde solution (19.5 g, 0.24 mole) is added to the reaction mixture simultaneously at 80°-85° C. The reaction mixture is stirred for 6 hours at 80°-85° C., cooled to room temperature and extracted with hexanes. The extracts are combined and fractionally distilled to yield the title product, identified by NMR analysis.

EXAMPLE 7

Preparation of 2-methoxymethylacrolein from 1,1,3-trimethoxypropane

To a mixture of 96% sulfuric acid (3.0 g, 0.024 mole), dibutylamine (6.7 g, 0.052 mole) and hydroquinone (1.6 g, 0.013 mole) in water at 85° C., is added a mixture of 1,1,3-trimethoxypropane (120.6 g, 0.90 mole) and 37% formaldehyde solution (84 g, 1.1 mole formaldehyde) over a 1.25 hour period. The reaction mixture is heated at reflux temperature for 5 hours, cooled to room temperature and extracted with methylene chloride. The extracts are combined and fractionally distilled to give the title product, identified by NMR analysis.

EXAMPLE 8

Preparation of 2-methoxymethylacrolein from β-methoxymethylpropionaldehyde

A mixture of β-methoxymethylpropionaldehyde (44 g, 0.43 mole), 37% formaldehyde (40.5 g, 0.52 mole), dibutylamine (6.8 g, 0.053 mole), 96% sulfuric acid (3.0 g, 0.029 mole) and hydroquinone (0.6 g, 0.055 mole) in water is heated at reflux temperature for 2 hours, cooled to room temperature and extracted with methylene chloride. The extracts are combined and fractionally distilled to give the title product, 20.5 g (48% yield), identified by NMR analysis.

EXAMPLE 9

Preparation of 2-alkoxymethylacrolein from β-alkoxymethylpropionaldehyde

Using essentially the same procedure described in Example 4 and substituting the appropriate β-alkoxymethylpropionaldehyde, the following compounds are obtained: 2-butoxymethylacrolein, 1.4 g (28% yield), identified by NMR analysis and 2-isopropoxymethylacrolein, 1.4 g (22% yield), identified by NMR analysis.

I claim:

1. A compound having the structural formula

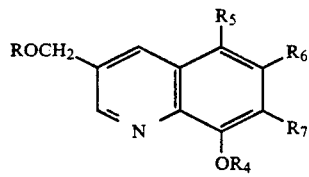

wherein
R is $C_1-C_6$alkyl;
R₄ is hydrogen or $C_1-C_4$alkyl; and
R₅, R₆ and R₇ are each independently hydrogen or OR₄.

2. The compound according to claim 1 wherein
R is $C_1-C_6$alkyl;
R₄ is hydrogen or $C_1-C_4$alkyl; and
R₅, R₆ and R₇ are each hydrogen;

3. The compound according to claim 2 wherein
R is methyl;
R₄ is hydrogen or $C_1-C_4$alkyl; and
R₄, R₆ and R₇ are each hydrogen.

4. The compound according to claim 3 3-(methoxymethyl)-8-quinolinol.

5. The compound according to claim 3 8-methoxy-3-(methoxymethyl)quinoline.

* * * * *

UNITED STATES PATENT AND TRADEMARK OFFICE
CERTIFICATE OF CORRECTION

PATENT NO. : 5,281,713

DATED : JANUARY 25, 1994

INVENTOR(S) : HENRY L. STRONG ET AL.

It is certified that error appears in the above-indentified patent and that said Letters Patent is hereby corrected as shown below:

Claim 3, Column 8, line 60: should read as follows:

--"3. The compound according to claim 2 wherein
R is methyl;
$R_4$ is hydrogen or $C_1$-$C_4$alkyl; and
$R_5$, $R_6$ and $R_7$ are each hydrogen.--

Signed and Sealed this

Seventeenth Day of December, 1996

Attest:

BRUCE LEHMAN

*Attesting Officer*  *Commissioner of Patents and Trademarks*